United States Patent
Na et al.

(10) Patent No.: US 11,946,070 B2
(45) Date of Patent: *Apr. 2, 2024

(54) METHOD OF REINFORCING EFFICACY OF STEM CELLS USING ETHIONAMIDE

(71) Applicant: SAMSUNG LIFE PUBLIC WELFARE FOUNDATION, Seoul (KR)

(72) Inventors: Duk Lyul Na, Seoul (KR); Jong Wook Chang, Seoul (KR); Hyo Jin Son, Seoul (KR)

(73) Assignee: SAMSUNG LIFE PUBLIC WELFARE FOUNDATION, Seoul (KR)

( * ) Notice: Subject to any disclaimer, the term of this patent is extended or adjusted under 35 U.S.C. 154(b) by 542 days.

This patent is subject to a terminal disclaimer.

(21) Appl. No.: 17/054,939

(22) PCT Filed: Jul. 15, 2020

(86) PCT No.: PCT/KR2020/009312
§ 371 (c)(1),
(2) Date: Nov. 12, 2020

(87) PCT Pub. No.: WO2021/010745
PCT Pub. Date: Jan. 21, 2021

(65) Prior Publication Data
US 2021/0261915 A1 Aug. 26, 2021

(30) Foreign Application Priority Data

Jul. 15, 2019 (KR) .................. 10-2019-0085137
Jul. 14, 2020 (KR) .................. 10-2020-0086685

(51) Int. Cl.
*C12N 5/0735* (2010.01)
*A61K 35/51* (2015.01)
*A61K 35/545* (2015.01)
*A61P 25/28* (2006.01)
*A61P 29/00* (2006.01)
*C12N 5/0775* (2010.01)

(52) U.S. Cl.
CPC ............ *C12N 5/0606* (2013.01); *A61K 35/51* (2013.01); *A61K 35/545* (2013.01); *A61P 25/28* (2018.01); *A61P 29/00* (2018.01); *C12N 5/0665* (2013.01); *C12N 2501/999* (2013.01)

(58) Field of Classification Search
CPC ... C12N 5/0606; C12N 5/0696; C12N 5/0665
See application file for complete search history.

(56) References Cited

U.S. PATENT DOCUMENTS

2015/0118748 A1* 4/2015 Ra .................. C12N 5/0667 435/325
2015/0232810 A1* 8/2015 Luo .................. A61P 25/00 435/377

FOREIGN PATENT DOCUMENTS

| KR | 10-2018-0044801 A | 5/2018 | |
|---|---|---|---|
| KR | 10-2019-0047880 A | 5/2019 | |
| WO | WO-2015009884 A1 * | 1/2015 | ........... C12N 5/0606 |
| WO | WO-2018/015945 A2 | 1/2018 | |
| WO | WO-2019/088480 A2 | 5/2019 | |

OTHER PUBLICATIONS

Dai et al. HIF-1α induced-VEGF overexpression in bone marrow stem cells protects cardiomyocytes against ischemia. Journal of Molecular and Cellular Cardiology 2007, 42:1036-1044. (Year: 2007).*
D. Zhang, G-C. Fan, X. Zhou, et al.; "Over-expression of CXCR4 on mesenchymal stem cells augments myoangiogenesis in the infarcted myocardium;" published in Journal of Molecular and Cellular Cardiology 44, pp. 281-292, 2008.
J. Wei, F. Cai, F. Wang, et al.; "Transplantation of CXCR4 Overexpressed Mesenchymal Stem Cells Augments Regeneration in Degenerated Intervertebral Discs;" DNA and Cell Biology, pp. 241-248, 2016. http://doi.org/10.1089/dna.2015.3118.
A. Barhanpurkar-Naik, S. Mhaske, S. Pote, et al.; "Interleukin-3 enhances the migration of human mesenchymal stem cells by regulating expression of CXCR4;" Stem Cell and Research Therapy, 2017.
Z. Cheng, L. Ou, X. Zhou, et al.; "Targeted Migration of Mesenchymal Stem Cells Modified with CXCR4 Gene to Infarcted Myocardium Improves Cardiac Performance;" The American Society of Gene Therapy, pp. 571-579, 2008.
X. Yu, D. Chen, Y. Zhang, et al.; "Overexpression of CXCR4 in mesenchymal stem cells promotes migration, neuroprotection and angiogenesis in a rat model of stroke;" Published in Journal of Neurological Sciences 316, pp. 141-149, 2012.
X. Liu, D. Zuo, H. Fan, et al.; "Over-expression of CXCR4 on mesenchymal stem cells protect against experimental colitis via immunomodulatory functions in impaired tissue;" Springer Science + Business Media Dordrecht; J Mol Hist 45, pp. 181-193, 2014.
International Search Report from corresponding PCT Application No. PCT/KR2020/009312, dated Dec. 28, 2020.

(Continued)

*Primary Examiner* — Allison M Fox
*Assistant Examiner* — Jennifer S Spence
(74) *Attorney, Agent, or Firm* — Harness, Dickey & Pierce, P.L.C.

(57) ABSTRACT

The present invention relates to a medium composition for reinforcing the efficacy of stem cells, including ethionamide, a method of reinforcing the efficacy of stem cells, including culturing stem cells in the medium composition, a method of preparing stem cells with reinforced efficacy, stem cells prepared by the above-mentioned method, and a use thereof. According to the present invention, the anti-inflammatory effect of mesenchymal stem cells and expression levels of paracrine factors may be effectively improved by a simple method of treating mesenchymal stem cells with ethionamide, and the stem cells obtained by the above method may be effectively used for preventing or treating an inflammatory disease or a degenerative brain disease.

3 Claims, 12 Drawing Sheets

(56) References Cited

OTHER PUBLICATIONS

Written Opinion of the International Searching Authority from corresponding PCT Application No. PCT/KR2020/009312, dated Dec. 28, 2020.
Park, et al. (2012) "Treatment Strategy for Parkinsonian Diseases Through Mesenchymal Stem Cells.", *Hanyang Med. Rev.*, 32:145-153. http://dx.doi.org/10.7599/hmr.2012.32.3.145.
Office Action from corresponding Japanese Patent Application No. 2022-502529, dated Dec. 23, 2022.
Haider Husnain K et al: "IGF-1-Overexpressing Mesenchymal Stern Cells Accelerate Bone Marrow Stem Cell Mobilization via Paracrine Activation of SDF-1 [alpha]/CXCR4 Signaling to Promote Myocardial Repair", Circulation Research, vol. 103, No. 11, Nov. 21, 2008 (Nov. 21, 2008), pp. 1300-1308, XP093045803, US.
Lee Na-Hee et al: "Ethionamide Preconditioning Enhances the Proliferation and Migration of Human Wharton's Jelly- Derived Mesenchymal Stem Cells", International Journal of Molecular Sciences, vol. 21, No. 19, Sep. 23, 2020 (Sep. 23, 2020), p. 7013, XP055818853, DOI: 10.3390/ijms21197013.

* cited by examiner

METHOD OF REINFORCING EFFICACY OF STEM CELLS USING ETHIONAMIDE

CROSS-REFERENCE TO RELATED APPLICATIONS

This application is a national phase application of PCT Application No. PCT/KR2020/009312, filed on Jul. 15, 2020, which claims priority to Korean Patent Application Nos. 10-2020-0086685, filed on Jul. 14, 2020 and 10-2019-0085137, filed on Jul. 15, 2019. The entire disclosure of the applications identified in this paragraph is incorporated herein by references.

FIELD

The present invention relates to a medium composition for reinforcing the efficacy of stem cells, which includes ethionamide, a method of reinforcing the efficacy of stem cells, which includes culturing stem cells in the medium composition, a method of preparing stem cells with reinforced efficacy, stem cells prepared by the method, and a use thereof.

BACKGROUND

Inflammation is one of the biological reactions to harmful stimuli of biological tissues such as pathogens and damaged cells, and a protective response involving immune cells, blood vessels and molecular biological intermediates. However, abnormal inflammation is associated with various human diseases, and provides the causes of various diseases such as an allergy, atopy, arthritis, a heart disease, a brain disease, a circulatory disorder, and cancer. The occurrence of various inflammatory diseases is associated with the activation of macrophages, which leads to excessive production of inflammatory factors, and the representative inflammatory factors include interleukin-1ß (IL-1ß), tumor necrosis factor-α (TNF-α) and nitric oxide (NO).

Degenerative brain diseases represented by Alzheimer's disease and Parkinson's disease are emerging as a serious social problem due to rapid aging. According to data from the Alzheimer's Association, it is predicted that Alzheimer's disease, which occurs every 68 seconds in the United States, will occur every 33 seconds in 2050. Alzheimer's disease is the third most expensive disease to treat, following heart disease and cancer, in the United States, and the sixth major cause of death throughout all age groups, and the fifth major cause of death for elderly people over 65. In Korea, it is estimated that the number of dementia patients will increase from 470,000 (8.8% of the population aged 65 and older) in 2010 to 750,000 (9.7%) in 2020, and cerebrovascular disease has been the second major cause of death in Korea for the past decade.

Recently, research results suggesting that excessive encephalopathy is a major cause of these degenerative brain diseases have been globally reported. Encephalopathy is one of the pathological symptoms that occur in most degenerative brain diseases such as Alzheimer's disease and Parkinson's disease, and the death of nerve cells is promoted by inflammatory mediators such as inflammatory cytokines or oxidizing materials produced from immune cells because of encephalopathy. Therefore, research on treating degenerative brain diseases by inhibiting encephalopathy is actively being conducted.

Meanwhile, mesenchymal stem cells are known as cells involved in tissue regeneration, treatment and immune responses as well as having multipotency, and therefore, efforts have been consistently made to isolate and culture mesenchymal stem cells from umbilical cord blood or bone marrow for developing therapeutic agents for various diseases using the above-described characteristics. For example, the mesenchymal stem cells are emerging as a new alternative for the treatment of autoimmune diseases, and their immunosuppressive and anti-inflammatory effects and T cell activation and proliferation inhibitory effects have been reported. In addition, the mesenchymal stem cells have been reported to exhibit a neuroprotective action, and secrete various nerve growth factors in a degenerative nervous system environment to contribute to the survival of nerve cells and the regeneration of nerve fibers, and since the mesenchymal stem cells have immunomodulatory ability, various immune responses are regulated. In addition, it is known that the degenerative nervous system environment is regulated as well as nerve regeneration through differentiation or fusion into nerve cells (Hanyang Med Rev 2012; 32:145-153).

However, since only the above-described effects of mesenchymal stem cells are known, and the development of mesenchymal stem cells optimized to have a more improved therapeutic effect has not been sufficiently developed, there is an urgent need for the development of stem cell therapeutic agents optimized by reinforced efficacy to treat an inflammatory disease and a degenerative brain disease.

SUMMARY

Technical Problem

Therefore, as a result of research on a method of further improving the anti-inflammatory effect of stem cells and the efficacy of expressing a paracrine factor, the inventors confirmed that the efficacy of stem cells is improved when ethionamide conventionally known as an antibiotic was treated, and the stem cells substantially reduce pathological symptoms of encephalopathy and dementia in vivo, and thus, the present invention was completed.

Therefore, the present invention is directed to providing a medium composition for reinforcing the efficacy of stem cells, which includes ethionamide.

In addition, the present invention is directed to providing a method of reinforcing the efficacy of stem cells, which includes culturing stem cells in the medium composition.

In addition, the present invention is directed to providing a method of preparing stem cells with reinforced efficacy, which includes culturing stem cells in the medium composition, stem cells with reinforced efficacy, prepared by the method, and a use of the stem cells.

However, technical problems to be solved in the present invention are not limited to the above-described problems, and other problems which are not described herein will be fully understood by those of ordinary skill in the art from the following descriptions.

Technical Solution

The present invention provides a medium composition for reinforcing the efficacy of stem cells, which includes ethionamide.

In one embodiment of the present invention, the ethionamide may be included in a medium at a concentration of 1 to 200 µM.

In another embodiment of the present invention, the stem cells may be embryonic stem cells or adult stem cells.

In still another embodiment of the present invention, the adult stem cells may be mesenchymal stem cells derived from one or more types of tissue selected from the group consisting of the umbilical cord, umbilical cord blood, bone marrow, fat, muscle, skin, the amnion and the placenta.

In yet another embodiment of the present invention, the enhancement in efficacy may be the improved expression of a paracrine factor in stem cells.

In yet another embodiment of the present invention, the paracrine factor may be one or more selected from the group consisting of a brain-derived neurotrophic factor (BDNF), a vascular endothelial cell growth factor (VEGF), insulin-like growth factor-1 (IGF-1), a hepatocyte growth factor (HGF), heme oxygenase-1 (HO-1), NAD(P)H:quinone oxidoreductase (NQO1), a glutamate-cysteine ligase catalytic subunit (GCLC) and a glutamate-cysteine ligase modifier subunit (GCLM).

In addition, the present invention provides a method of reinforcing the efficacy of stem cells, which includes culturing stem cells in the medium composition.

In addition, the present invention provides a method of preparing stem cells with reinforced efficacy, which includes culturing stem cells in the medium composition.

In addition, the present invention provides stem cells with reinforced efficacy, which are prepared by the above-described method.

In addition, the present invention provides a pharmaceutical composition for preventing or treating an inflammatory disease, which includes the stem cells as an active ingredient.

In one embodiment of the present invention, the inflammatory disease may be selected from the group consisting of dermatitis, allergies, atopy, asthma, conjunctivitis, periodontitis, rhinitis, otitis media, sore throats, tonsillitis, pneumonia, gastric ulcers, gastritis, Crohn's disease, colitis, peritonitis, osteomyelitis, cellulitis, meningitis, encephalitis, pancreatitis, stroke, acute bronchitis, chronic bronchitis, hemorrhoids, gout, ankylosing spondylitis, rheumatic fever, lupus, fibromyalgia, psoriatic arthritis, osteoarthritis, rheumatoid arthritis, infectious arthritis, periarthritis, tendinitis, tenosynovitis, peritendinitis, myositis, hepatitis, cystitis, nephritis, Sjogren's syndrome, multiple sclerosis, and acute and chronic inflammatory diseases.

In addition, the present invention provides a method of preventing or treating an inflammatory disease, which includes treating a subject with the pharmaceutical composition including the stem cells as an active ingredient.

In addition, the present invention provides a use of the pharmaceutical composition for preventing or treating an inflammatory disease.

In addition, the present invention provides a pharmaceutical composition for preventing or treating a degenerative brain disease, which includes the stem cells as an active ingredient.

In one embodiment of the present invention, the degenerative brain disease may be selected from the group consisting of Parkinson's disease, dementia, Alzheimer's disease, frontotemporal dementia, Huntington's disease, stroke, cerebral infarction, Pick's disease, a head injury, a spinal cord injury, cerebral arteriosclerosis, Lou Gehrig's disease, multiple sclerosis, senile depression and Creutzfeldt-Jakob disease.

In addition, the present invention provides a method of preventing or treating a degenerative brain disease, which includes treating a subject with the pharmaceutical composition including the stem cells as an active ingredient.

In addition, the present invention provides a use of the pharmaceutical composition for preventing or treating a degenerative brain disease.

Advantageous Effects

The inventors experimentally confirmed that, when inflammation-induced microglial cells were co-cultured with ethionamide-primed mesenchymal stem cells, an anti-inflammatory effect caused by mesenchymal stem cells is improved, and the paracrine activity of various growth factors and antioxidant factors are improved in ethionamide-primed mesenchymal stem cells, and further confirmed an effect of substantially reducing amyloid beta, encephalopathy and phosphorylated tau by administration of the mesenchymal stem cells in a dementia animal model. Therefore, according to the present invention, the anti-inflammatory effect of mesenchymal stem cells and the expression level of paracrine factors can be effectively improved by a simple process of treating mesenchymal stem cells with ethionamide, and the stem cells prepared by the above-mentioned method can be effectively used for preventing or treating an inflammatory disease or degenerative brain disease.

DETAILED DESCRIPTION

Figure 1A:
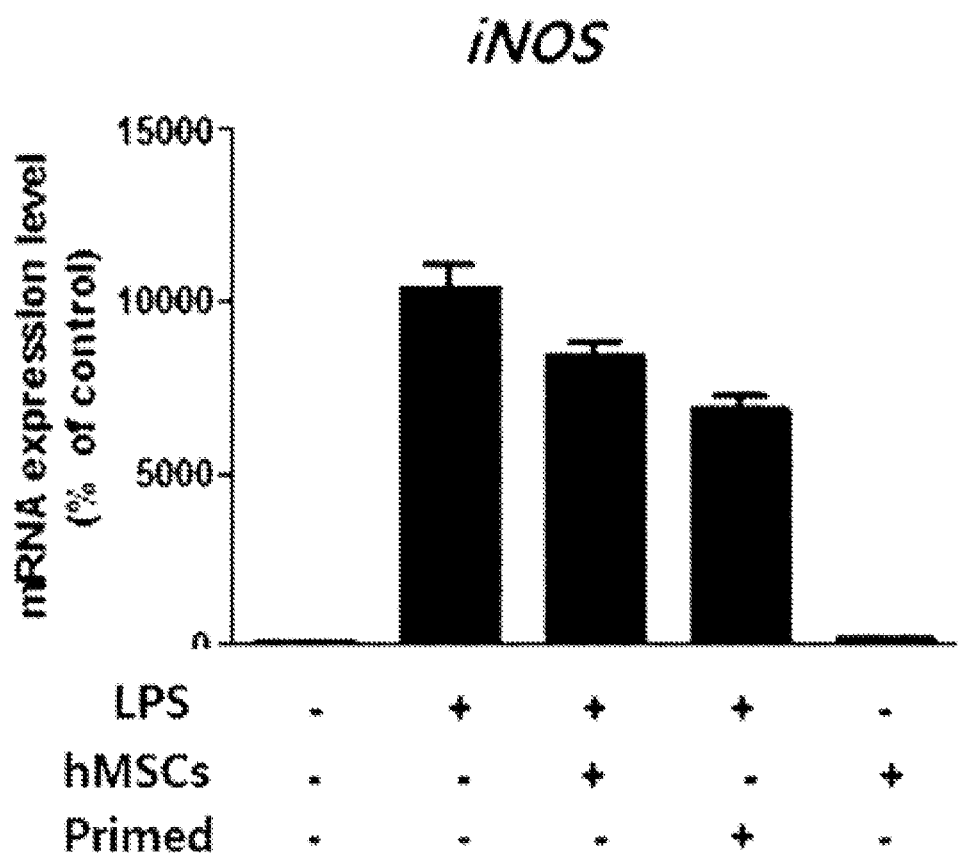
FIG. 1A shows iNOS expression levels after inflammation-induced microglial cells (BV2) and ethionamide-primed or unprimed mesenchymal stem cells are co-cultured.

The present invention provides a medium composition for reinforcing the efficacy of stem cells, which includes ethionamide.

Conventionally, 2-ethylpyridine-4-carbothioamide (ethionamide) having the following chemical structure is a thionamide-based antibiotic and was known for treatment of a bacterial infection disease, but in the present invention, an ethionamide effect for reinforcing the efficacy of stem cells was first found.

[Ethionamide]

The inventors confirmed the effect of reinforcing the efficacy of ethionamide-primed stem cells through specific examples.

In one embodiment of the present invention, as a result of measuring iNOS, NO and ROS levels after inflammation-induced microglial cells and ethionamide-primed or unprimed mesenchymal stem cells are co-cultured, in the group co-cultured with ethionamide-primed mesenchymal stem cells, compared with a control or ethionamide-unprimed group, the expression of the factors may be further reduced, showing that the anti-inflammatory effect of the mesenchymal stem cells is improved by ethionamide treatment (see Example 3).

In another embodiment of the present invention, as a result of measuring expression levels of inflammatory cytokines, IL-6 and TNF-α, after inflammation-induced microglial cells and ethionamide-primed or unprimed mesenchymal stem cells are co-cultured, it was confirmed that inhibitory effects on the expression of the inflammatory cytokines are improved in the group co-cultured with ethionamide-primed mesenchymal stem cells, compared with a control or ethionamide-unprimed group (see Example 4).

In still another embodiment of the present invention, as a result of measuring NF-κB activity after inflammation-induced microglial cells and ethionamide-primed or unprimed mesenchymal stem cells are co-cultured, inhibitory effects on NF-κB activity are improved in the group co-cultured with ethionamide-primed mesenchymal stem cells, compared with a control or ethionamide-unprimed group (see Example 5).

In yet another embodiment of the present invention, as a result of treating mesenchymal stem cells with ethionamide by concentration and measuring secretion amounts of various growth factors and antioxidant factors, it was confirmed that the expression level of the paracrine factor increases in proportion to the treatment concentration of ethionamide (see Example 6).

In yet another embodiment of the present invention, the in vivo effect of ethionamide-primed stem cells is confirmed. Particularly, as a result of immunostaining or ELISA performed after ethionamide-primed or unprimed mesenchymal stem cells are administered to a ventricle of a dementia mouse model and brain tissue is then extracted, it is confirmed that the ethionamide-primed mesenchymal stem cells have a significant effect of reducing amyloid β, encephalopathy and phosphorylated tau protein (see Examples 7 to 9).

Thus, the above results show that the efficacy of human mesenchymal stem cells can be further improved by ethionamide treatment.

The concentration of ethionamide included in a medium in the present invention may be, but is not limited to, 1 to 200 μM, and preferably, 50 to 200 μM, and more preferably, 50 to 150 μM.

The term "stem cell" used herein is an undifferentiated cell, having a self-replication capability and the ability to differentiate into two or more different types of cells. The stem cell of the present invention may be autologous or allogeneic stem cells, may be derived from any type of animal including a human and a non-human mammal, and may be derived from an adult or embryo, but the present invention is not limited thereto.

In the present invention, adult stem cells derived from the adult may be mesenchymal stem cells, human tissue-derived mesenchymal stromal cells, human tissue-derived mesenchymal stem cells, multipotent stem cells or amniotic epithelial cells, and preferably, mesenchymal stem cells, but the present invention is not limited thereto. The mesenchymal stem cells may be mesenchymal stem cells derived from the umbilical cord, umbilical cord blood, bone marrow, fat, muscle, nerve, skin, the amnion and the placenta, but the present invention is not limited thereto.

In the present invention, the isolation and culture of mesenchymal stem cells may be performed by a method well known to those of ordinary skill in the art, and there is no limitation on the method as long as it can proliferate mesenchymal stem cells without changing characteristics thereof while maintaining stem ness.

The reinforced efficacy of stem cells in the present invention refers to the improvement in therapeutic properties and effect of stem cells against an inflammatory disease or a degenerative brain disease, and more particularly, improvement in inhibition of the generation of nitric oxide, a related factor thereof or reactive oxygen species, inhibition of the expression of an inflammatory cytokine, anti-oxidative and anti-inflammatory effects according to the reduction in NF-κB activity, and the improvement in efficacy of expressing paracrine factors such as a growth factor and an antioxidative factor.

The paracrine factor is more specifically one or more selected from the group consisting of a brain-derived neurotrophic factor (BDNF), a vascular endothelial cell growth factor (VEGF), insulin-like growth factor-1 (IGF-1), a hepatocyte growth factor (HGF), heme oxygenase-1 (HO-1), NAD(P)H:quinone oxidoreductase (NQO1), a glutamate-cysteine ligase catalytic subunit (GCLC) and a glutamate-cysteine ligase modifier subunit (GCLM), but the present invention is not limited thereto.

As another aspect of the present invention, the present invention provides a method of reinforcing the efficacy of stem cells, which includes culturing stem cells in the medium composition.

As still another aspect of the present invention, the present invention provides a method of preparing stem cells with reinforced efficacy, which includes culturing stem cells in the medium composition.

In addition, the present invention provides stem cells with reinforced efficacy, prepared by the above-described method.

As yet another aspect of the present invention, the present invention provides an anti-inflammatory composition, which includes the stem cells as an active ingredient.

As yet another aspect of the present invention, the present invention provides a pharmaceutical composition for preventing or treating an inflammatory disease or degenerative brain disease, which includes the stem cells as an active ingredient.

The term "prevention" used herein refers to all actions of inhibiting or delaying the onset of an inflammatory disease or degenerative brain disease by administration of the pharmaceutical composition according to the present invention.

The term "treatment" used herein refers to all actions involved in alleviating or beneficially changing symptoms of an inflammatory disease or degenerative brain disease by administration of the pharmaceutical composition according to the present invention.

The term "inflammatory disease" used herein is the generic term for diseases with inflammation as a main lesion, and more preferably, in the present invention, the inflammatory disease may be selected from the group consisting of dermatitis, allergies, atopy, asthma, conjunctivitis, periodontitis, rhinitis, otitis media, sore throats, tonsillitis, pneumonia, gastric ulcers, gastritis, Crohn's disease, colitis, peritonitis, osteomyelitis, cellulitis, meningitis, encephalitis, pancreatitis, stroke, acute bronchitis, chronic bronchitis, hemorrhoids, gout, ankylosing spondylitis, rheumatic fever, lupus, fibromyalgia, psoriatic arthritis, osteoarthritis, rheumatoid arthritis, infectious arthritis, periarthritis, tendinitis, tenosynovitis, peritendinitis, myositis, hepatitis, cystitis, nephritis, Sjogren's syndrome, multiple sclerosis, and acute and chronic inflammatory diseases, but the present invention is not limited thereto.

The term "degenerative brain disease" used herein is a disease occurring in the brain among degenerative diseases occurring with age, and more preferably, the degenerative brain disease in the present invention may be selected from the group consisting of Parkinson's disease, dementia, Alzheimer's disease, frontotemporal dementia, Huntington's disease, stroke, cerebral infarction, Pick's disease, a head injury, a spinal cord injury, cerebral arteriosclerosis, Lou Gehrig's disease, multiple sclerosis, senile depression and Creutzfeldt-Jakob disease, but the present invention is not limited thereto.

The pharmaceutical composition according to the present invention may include stem cells with reinforced efficacy by ethionamide treatment, and further include a pharmaceutically acceptable carrier. The pharmaceutically acceptable carrier is conventionally used in formulation, and includes saline, distilled water, Ringer's solution, buffered saline, cyclodextrin, a dextrose solution, a maltodextrin solution, glycerol, ethanol, liposomes, etc., but the present invention is not limited thereto. If needed, the pharmaceutically composition may further include other conventional additives including an antioxidant, a buffer, etc. In addition, by additionally adding a diluent, a dispersant, a surfactant, a binder or a lubricant, the pharmaceutical composition may be formulated as an injectable form such as an aqueous solution, an emulsion or a suspension, a pill, a capsule, a granule or a tablet. Suitable pharmaceutically acceptable carriers and their formulations may be formulated according to each ingredient using a method disclosed in Remington's Pharmaceutical Science. The pharmaceutical composition of the present invention is not limited in dosage form, and thus may be formulated as an injection, an inhalant or a dermal preparation for external use.

The pharmaceutical composition of the present invention may be administered orally or parenterally (e.g., intravenously, subcutaneously, intraperitoneally or topically), and preferably, intracerebrally, according to a desired method, and a dose of the pharmaceutical composition of the present invention may be suitably selected according to a patient's condition and body weight, severity of a disease, a dosage form, an administration route and duration by those of ordinary skill in the art.

The pharmaceutical composition according to the present invention is administered at a pharmaceutically effective amount. In the present invention, the "pharmaceutically effective amount" used herein refers to an amount sufficient for treating a disease at a reasonable benefit/risk ratio applicable for medical treatment, and an effective dosage may be determined by parameters including a type of a patient's disease, severity, drug activity, sensitivity to a drug, administration time, an administration route and an excretion rate, the duration of treatment and drugs simultaneously used, and other parameters well known in the medical field. The pharmaceutical composition of the present invention may be administered separately or in combination with other therapeutic agents, and may be sequentially or simultaneously administered with a conventional therapeutic agent, or administered in a single or multiple dose(s). In consideration of all of the above-mentioned parameters, it is important to achieve the maximum effect with the minimum dose without a side effect, and such a dose may be easily determined by those of ordinary skill in the art.

Specifically, the effective amount of the pharmaceutical composition of the present invention may be changed according to a patient's age, sex, condition, body weight, absorption of an active ingredient in the body, an inactivation rate and excretion rate, a disease type, and a drug used in combination, and generally, $5 \times 10^2$ cells to $5 \times 10^8$ cells per kg of body weight may be administered daily or every other day, or one to several times a day. For multiple administrations, administration may be performed every week or every month. However, the effective amount may be increased or decreased depending on the route of administration, the severity of obesity, sex, a body weight or age, and thus it does not limit the scope of the present invention in any way.

As another aspect of the present invention, the present invention provides a method of preventing or treating an inflammatory disease or degenerative brain disease, which includes administering the pharmaceutical composition to a subject.

The term "subject" used herein refers to a target in need of treatment, and more specifically, a mammal such as a human or a non-human primate, a mouse, a rat, a dog, a cat, a horse, or a cow.

In addition, the present invention provides a use of the pharmaceutical composition for preventing or treating an inflammatory disease or degenerative brain disease.

Hereinafter, to help in understanding the present invention, exemplary examples will be suggested. However, the following examples are merely provided to more easily understand the present invention, and not to limit the present invention.

EXAMPLES

Example 1. Preparation of Human Umbilical Cord Mesenchymal Stem Cells

Human umbilical cord mesenchymal stem cells were isolated by the following method, after the umbilical cord was obtained according to the criteria approved by IRB (IRB #2015-09-023-003) of the Samsung Medical Center.

First, a 3 to 4 cm piece of umbilical cord tissue was fragmented, and treated with a collagenase solution (Gibco, USA) for 60 to 90 minutes to digest an extracellular matrix, followed by digestion with 0.25% trypsin (Gibco, USA) for 30 minutes at 37° C. Subsequently, cells were obtained by adding fetal bovine serum (FBS; Biowest, USA) to the resulting product, and then performing centrifugation at 1000×g for 10 minutes, and then cultured using Minimum Essential Media (MEM; Gibco, USA) supplemented with 10% FBS and 50 μg/ml gentamycin (Gibco, USA) at 37° C. in a 5% CO2 atmosphere, and thus mesenchymal stem cells at passage 5 or 6 were used for an experiment.

Example 2. Preparation of Ethionamide-Primed Human Umbilical Cord Mesenchymal Stem Cells $6 \times 10^3$ cells/cm 2 of the human umbilical cord mesenchymal stem cells prepared according to the method of Example 1 were seeded in a cell culture container, and simultaneously, ethionamide was treated at a concentration of 50 μM, 100 μM or 150 μM, followed by culturing for 72 hours.

Example 3. Verification of Anti-Inflammatory Effect of Ethionamide-Primed Stem Cells To verify whether the anti-inflammatory effect of the stem cells is improved when mesenchymal stem cells were treated with ethionamide, an experiment was carried out as follows. Specifically, an inflammatory model was induced by treating microglial cells, BV2 cells, with lipopolysaccharide (LPS), and co-cultured with ethionamide-primed or unprimed mesenchymal stem cells (hMSCs), followed by measuring expression levels of nitric oxide (NO), NO-related factors and reactive oxygen species.

Figure 1B:
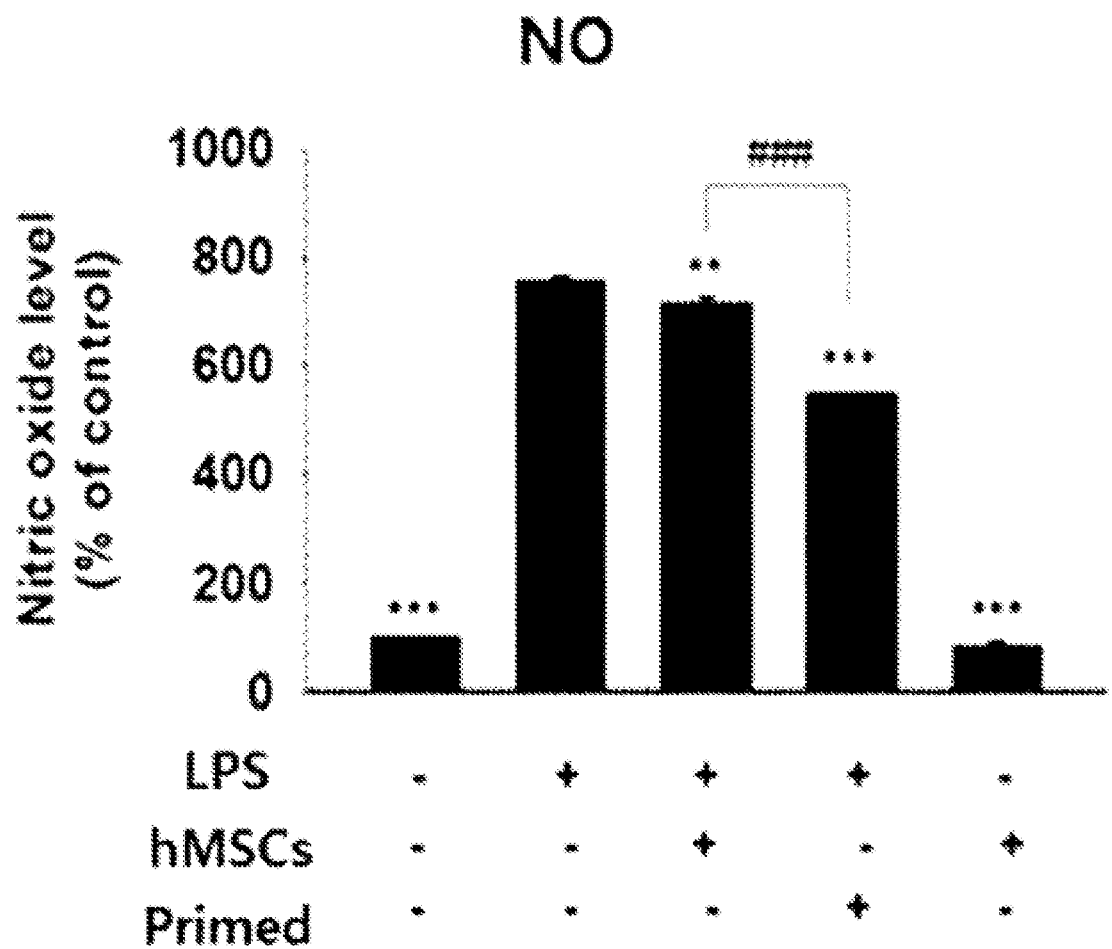
FIG. 1B shows NO expression levels after inflammation-induced microglial cells (BV2) and ethionamide-primed or unprimed mesenchymal stem cells are co-cultured.
Figure 1C:
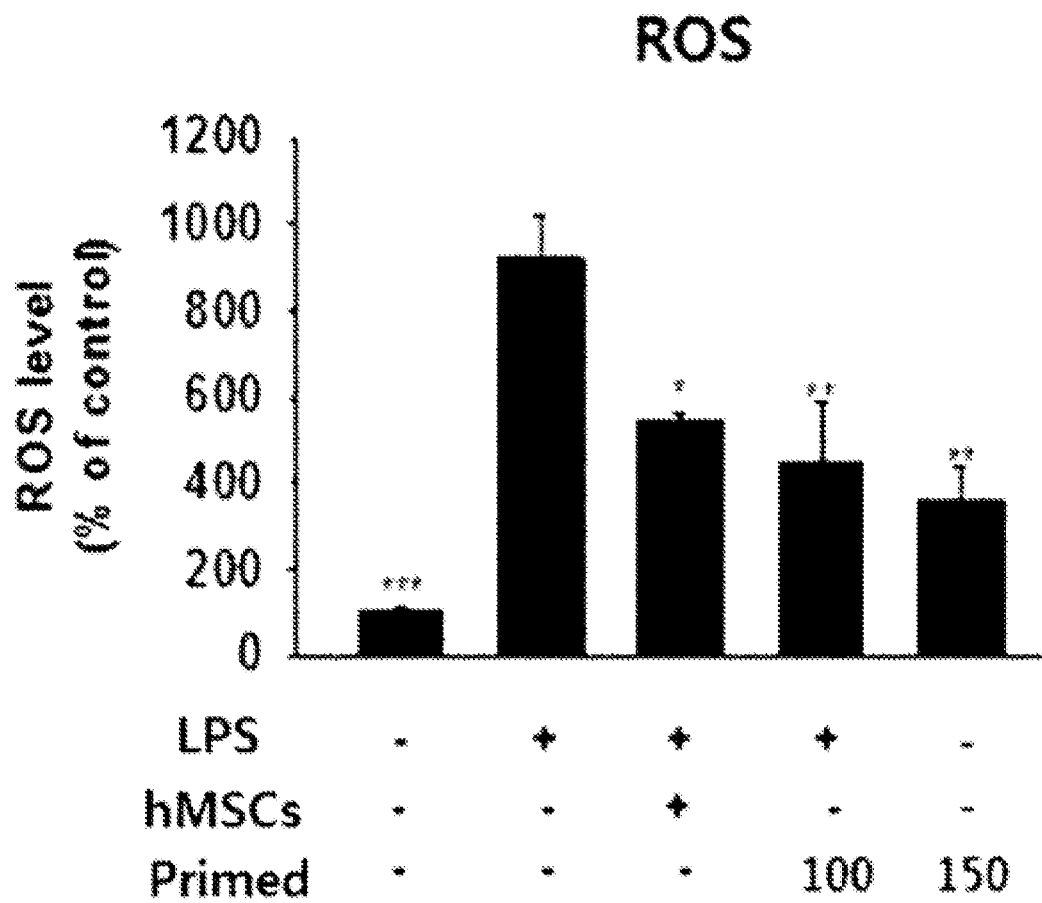
FIG. 1C shows ROS expression levels after inflammation-induced microglial cells (BV2) and ethionamide-primed or unprimed mesenchymal stem cells are co-cultured.

As a result, as shown in FIG. 1A, in the case of a representative NO-related inflammatory factor, inducible nitric oxide synthase (iNOS), compared with a control or the group co-cultured with ethionamide-unprimed mesenchymal stem cells, in the group co-cultured with ethionamide-primed mesenchymal stem cells, mRNA expression significantly decreased. In addition, according to the result of measuring NO and ROS expression levels, as shown in FIGS. 1B and 1C, compared with a control or the group co-cultured with ethionamide-unprimed mesenchymal stem cells, in the group co-cultured with ethionamide-primed mesenchymal stem cells, the expression levels were confirmed to significantly decrease. These results indicate that the anti-inflammatory effect of the stem cells is improved by treating mesenchymal stem cells with ethionamide.

Example 4. Verification of Effect of Inhibiting Cytokine Expression by Ethionamide-Primed Stem Cells Based on the results of Example 1, the inventors induced the same inflammatory model as in Example 1, and co-cultured it with ethionamide-primed or unprimed mesenchymal stem cells, followed by measuring expression levels of representative inflammatory cytokines, IL-6 and TNF-α.

Figure 2A:
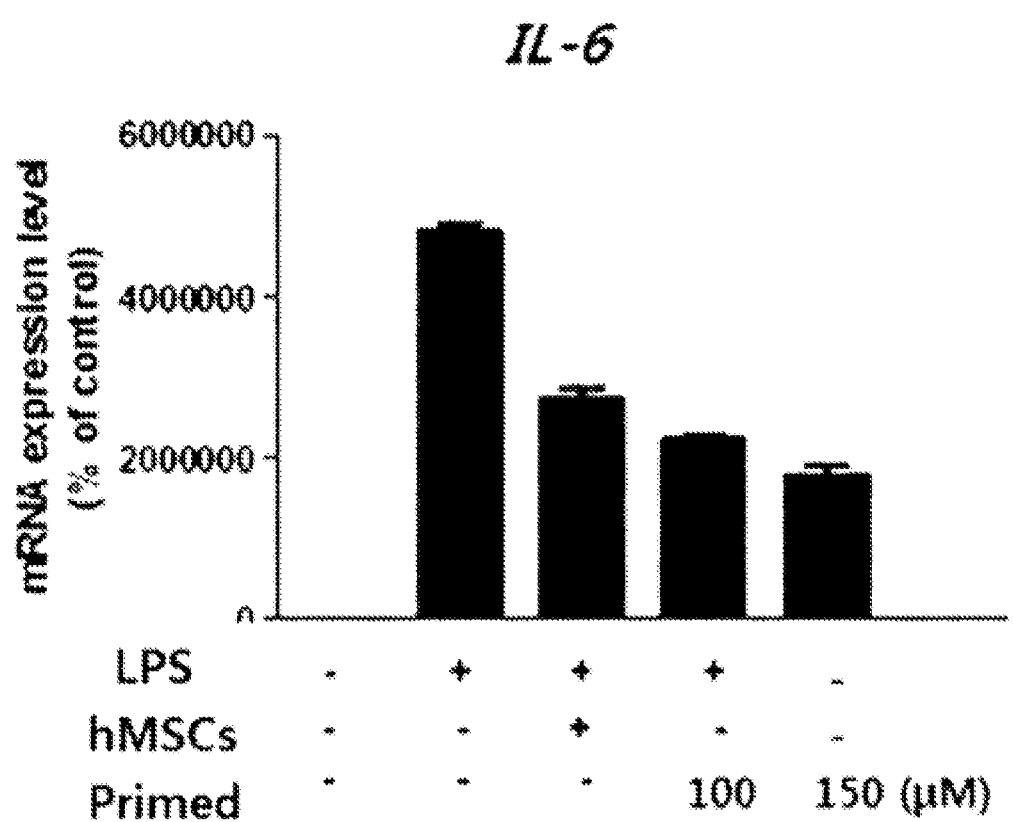
FIG. 2A shows mRNA expression levels of an inflammatory cytokine, IL-6, after inflammation-induced microglial cells (BV2) and ethionamide-primed or unprimed mesenchymal stem cells are co-cultured.
Figure 2B:
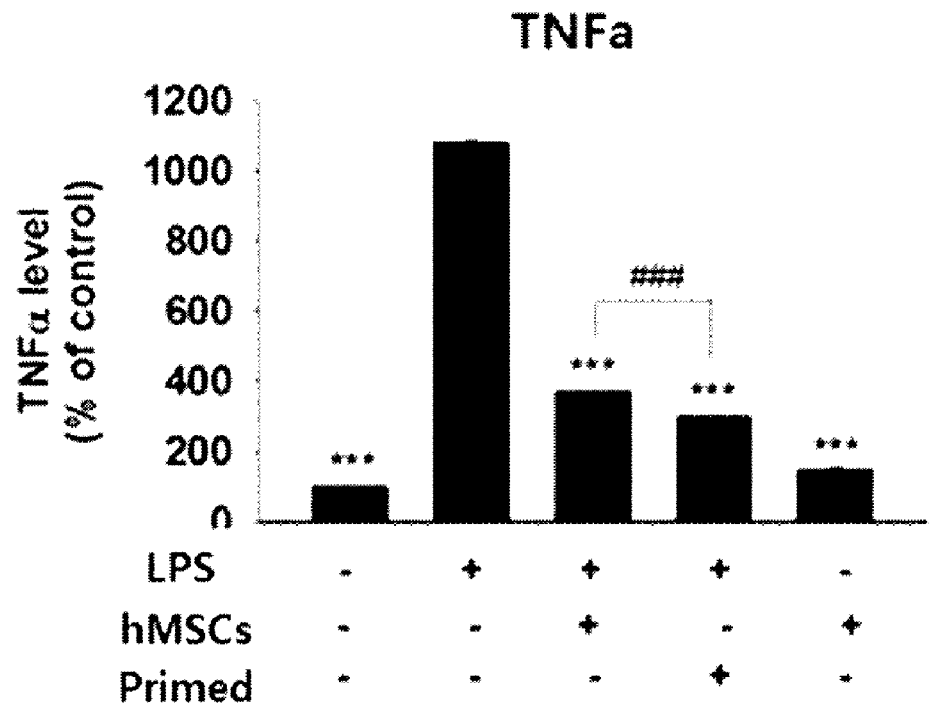
FIG. 2B shows mRNA expression levels of an inflammatory cytokine, TNF-α after inflammation-induced microglial cells (BV2) and ethionamide-primed or unprimed mesenchymal stem cells are co-cultured.
Figure 2B:
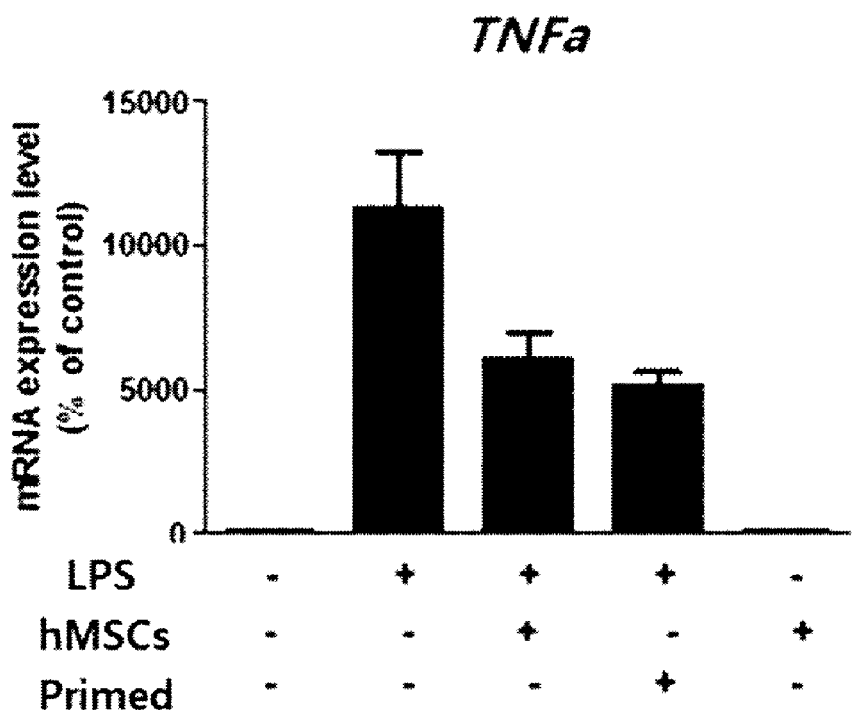

As a result, as shown in FIGS. 2A and 2B, compared with a control or the group co-cultured with ethionamide-unprimed mesenchymal stem cells, in the group co-cultured with ethionamide-primed stem cells, the expression of each of IL-6 and TNF-α mRNA slightly decreased, and the expression level of IL-6 decreased in proportion to a treated concentration of ethionamide (100 or 150 μM). In addition, as shown in FIG. 2B, as a result of measuring a TNF-α protein level by ELISA, it was confirmed that the group co-cultured with ethionamide-primed mesenchymal stem cells showed a significant decrease in protein level. These results indicate that the effect of inhibiting the expression of inflammatory cytokines in the stem cells is improved by treating mesenchymal stem cells with ethionamide.

Example 5. Verification of Effect of Inhibiting NF-κB Activity by Ethionamide-Primed Stem Cells Nuclear factor-κB (NF-κB) is known as the most important transcription factor involved in the mechanism of inflammation in immune cells, and abnormal NF-κB activation caused by various reasons is reported as a mechanism of developing various inflammatory diseases, including a degenerative brain disease. Therefore, based on the results of Examples 1 and 2, it was intended to verify whether ethionamide treatment can improve an effect of inhibiting NF-κB activity in mesenchymal stem cells. To this end, like Examples 1 and 2, after induction of inflammation, microglial cells BV2 were co-cultured with ethionamide-primed or unprimed mesenchymal stem cells, and the activity of NF-κB was measured.

Figure 3:
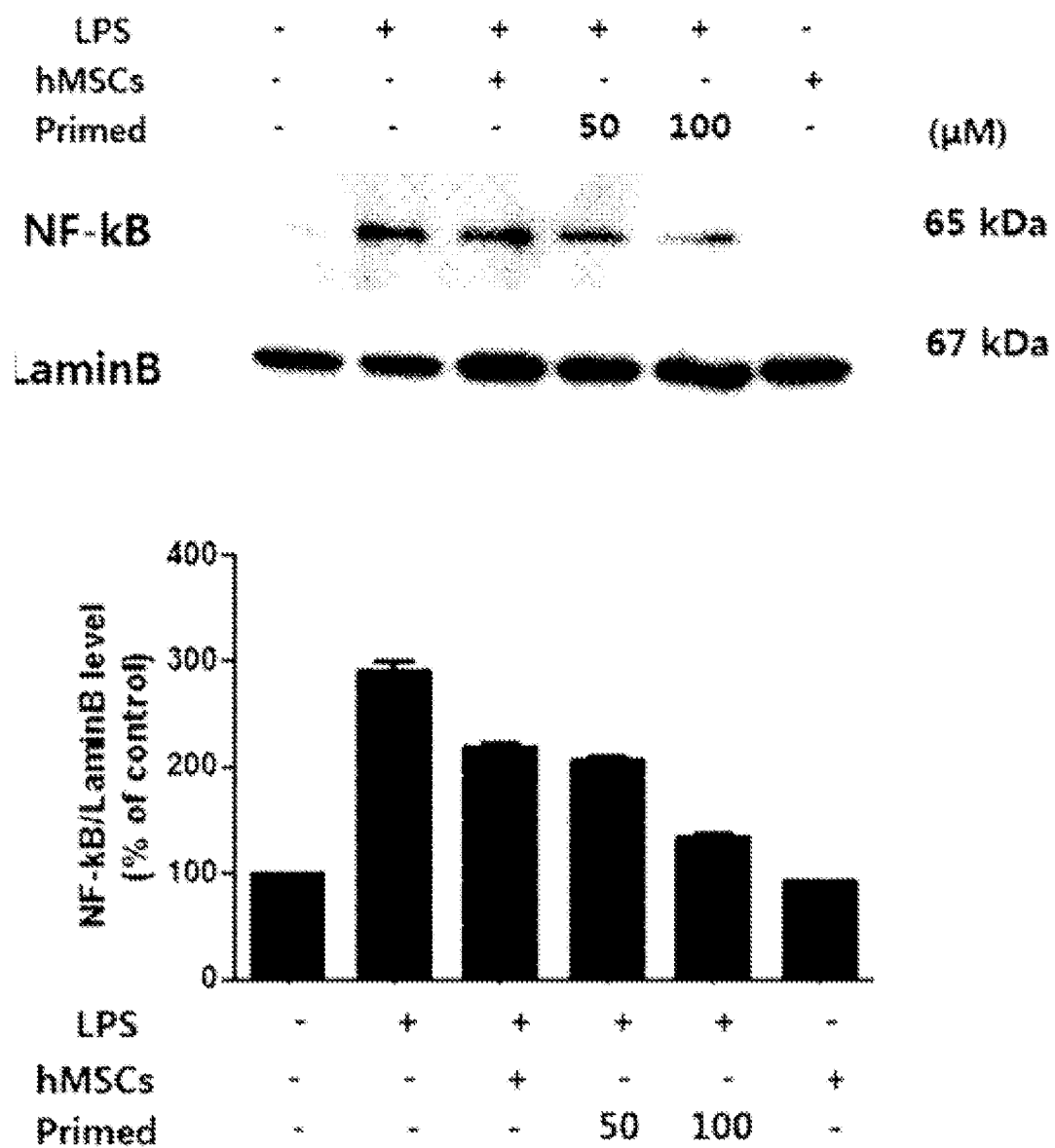
FIG. 3 shows NF-κB activity measured by western blotting and quantified expression levels thereof after inflammation-induced microglial cells (BV2) and ethionamide-primed or unprimed mesenchymal stem cells are co-cultured.

As a result, as shown in FIG. 3, compared with a control or the group co-cultured with ethionamide-unprimed mesenchymal stem cells, in the group co-cultured with ethionamide-primed mesenchymal stem cells, the expression of NF-κB protein decreased in proportion to a treated concentration of ethionamide (100 or 150 μM), and it was confirmed from the quantification result obtained by western blotting that the expression significantly decreases, compared with the control. These results indicate that the effect of inhibiting NF-κB activity by the stem cells is improved by treating mesenchymal stem cells with ethionamide.

Figure 4A:
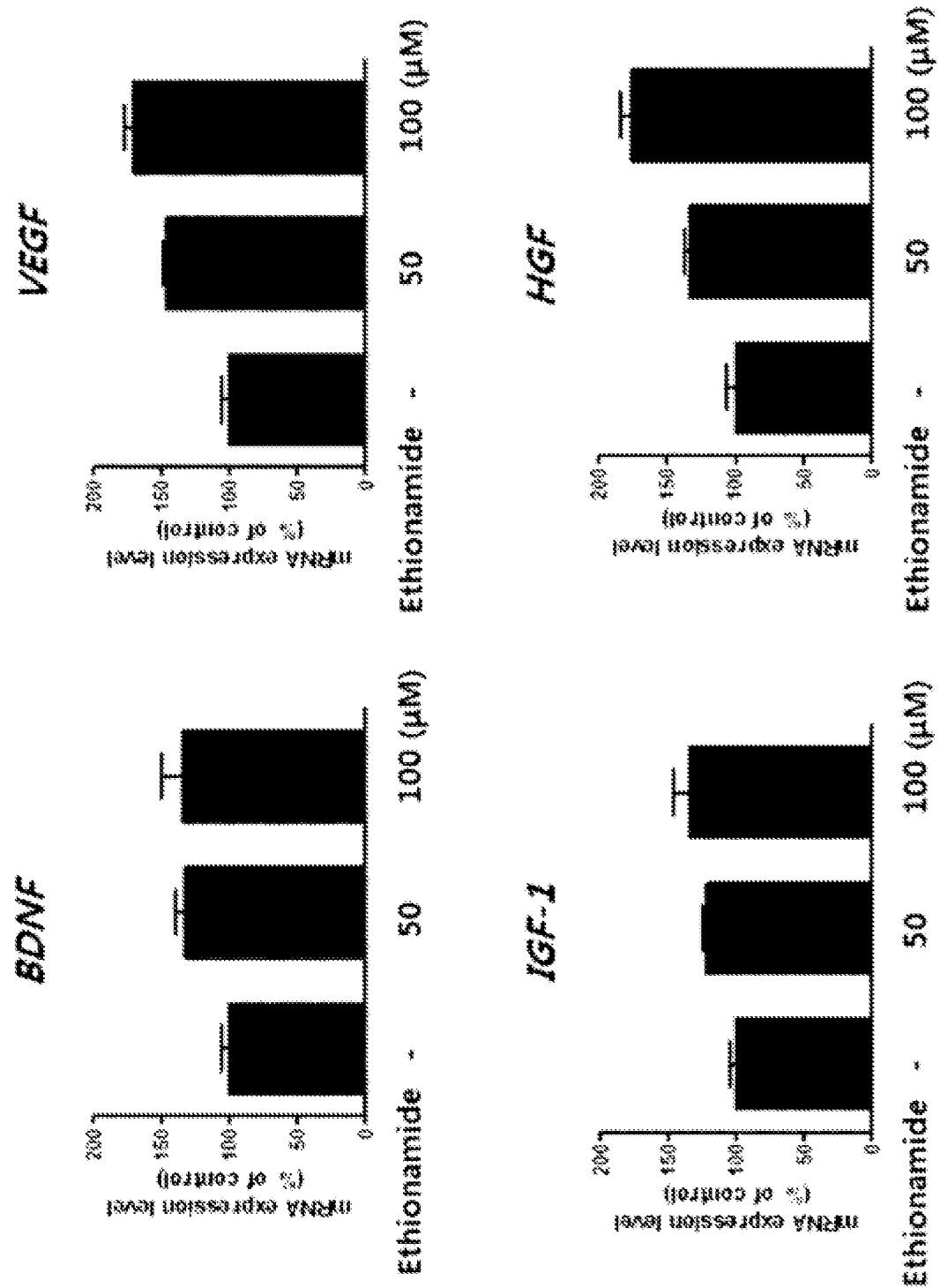
FIG. 4A shows expression levels of growth factors, BDNF, VEGF, IGF-1 and HGF, as paracrine factors, after mesenchymal stem cells were treated with ethionamide, by concentration (50 and 100 μM).

Example 6. Verification of Effect of Improving Paracrine Factor Expression by Ethionamide-Primed Stem Cells To verify whether the expression level of a paracrine factor of mesenchymal stem cells is changed by ethionamide treatment, the mesenchymal stem cells were treated with ethionamide at 50 or 100 μM, and then expression levels of a brain-derived neurotrophic factor (BDNF), a vascular endothelial cell growth factor (VEGF), insulin-like growth factor-1 (IGF-1) and a hepatocyte growth factor (HGF), which are known as paracrine factors, were measured. As a result, as shown in FIG. 4A, it was confirmed that the expression of the paracrine factors increases in proportion to the treated concentration of ethionamide.

Figure 4B:
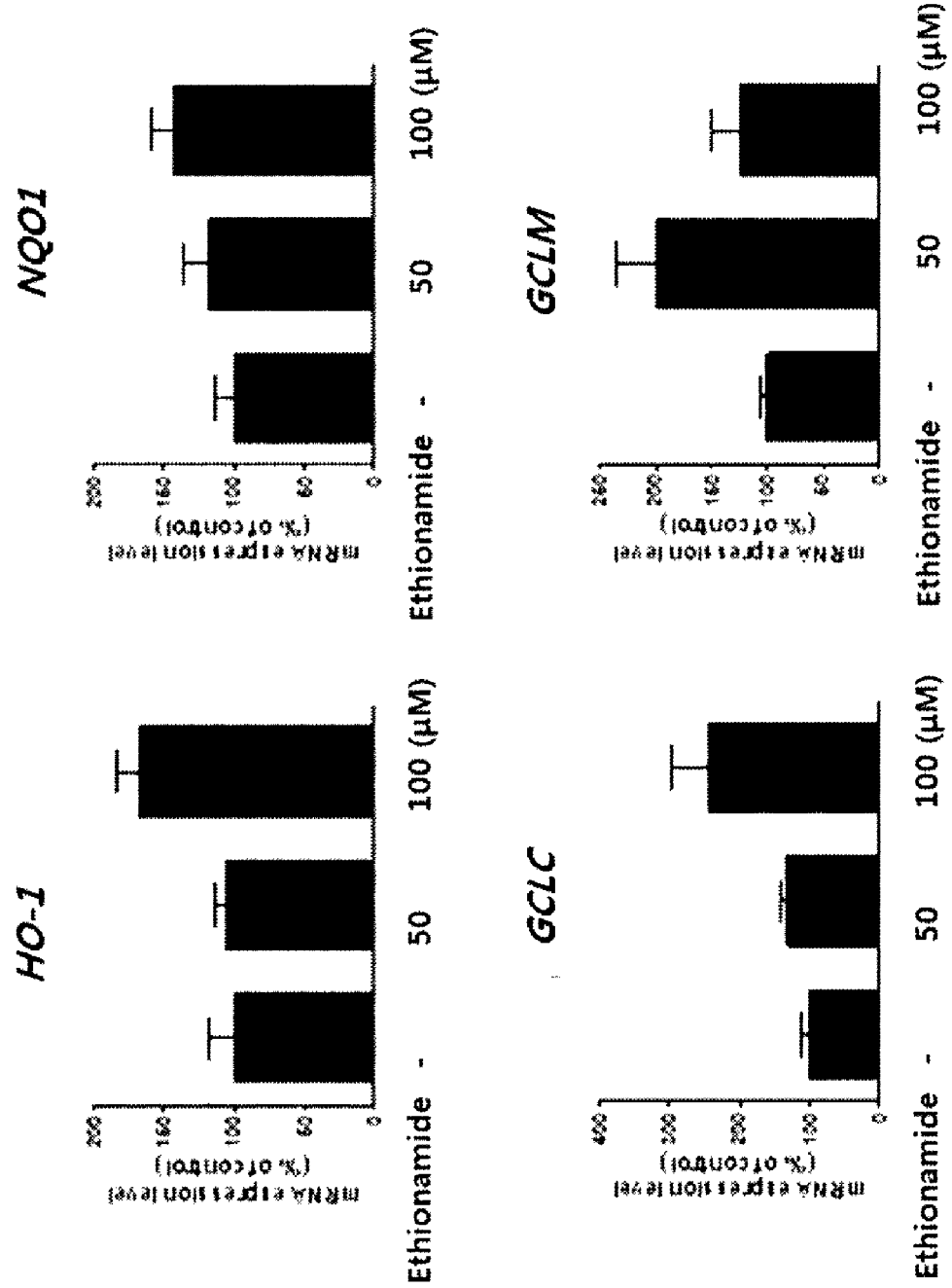
FIG. 4B shows expression levels of antioxidation-related factors, HO-1, NQO1, GCLC and GCLM, as paracrine factors, after mesenchymal stem cells were treated with ethionamide, by concentration (50 and 100 μM).

Subsequently, the mesenchymal stem cells were treated with ethionamide by the same method as described above, and mRNA expression levels of antioxidation-related factors, such as HO-1, NQO1, GCLC and GCLM were measured. As a result, as shown in FIG. 4B, it was confirmed that, in general, the expression of HO-1, NQO1, GCLC and GCLM genes in the mesenchymal stem cells significantly increases in proportion to the treated concentration of ethionamide.

These results indicate that the expression of paracrine factors of the stem cells is improved by treating mesenchymal stem cells with ethionamide.

Example 7. Confirmation of Amyloid 13 Reducing Effect by Ethionamide-Primed Stem Cells in Dementia Mouse Model To examine whether ethionamide-primed mesenchymal stem cells actually have a therapeutic effect on a degenerative brain disease, the inventors measured expression levels of amyloid 13 according to the administration of the mesenchymal stem cells using a dementia mouse model.

Specifically, in the dementia mouse model, ethionamide-primed or unprimed mesenchymal stem cells (hMSCs) were administered to a mouse ventricle, and the brain was then extracted one week after administration. The extracted brain was fixed with 4% paraformaldehyde, and then processed to obtain a tissue section, and the tissue section was treated with a representative antibody, anti-6E10, against amyloid 13 for immunostaining, followed by observing the tissue using a fluorescence microscope. In addition, fluorescence intensity was quantified and plotted on a graph.

Figure 5A:
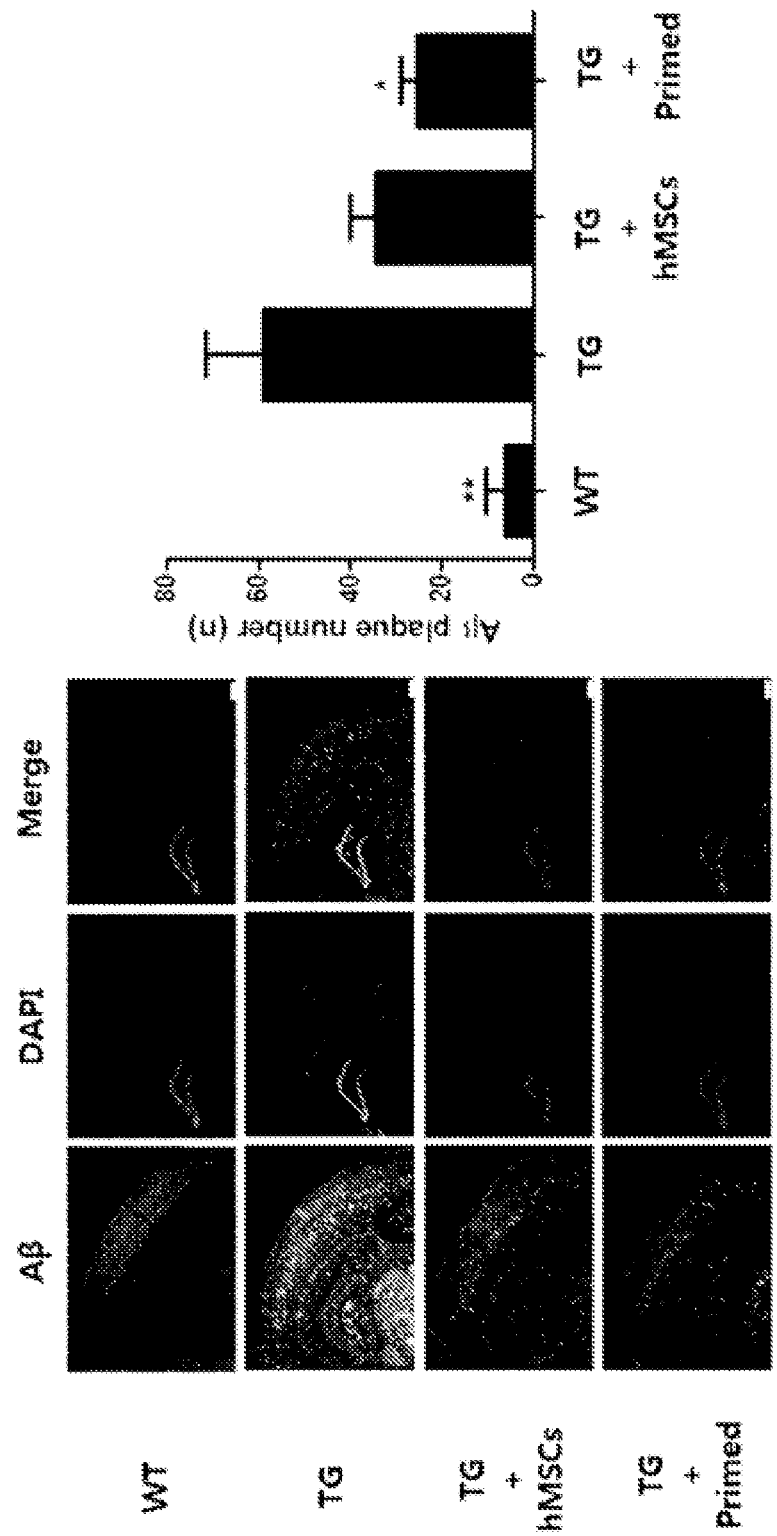
FIG. 5A shows results of immunostaining performed on brain tissue sections obtained one week after ethionamide-primed or unprimed mesenchymal stem cells are administered to a ventricle of a dementia mouse model using an amyloid 13 antibody (anti-6E10), and the quantification result thereof.

As a result, as shown in FIG. 5A, compared with a control or the group co-cultured with ethionamide-unprimed mesenchymal stem cells, in the group co-cultured with ethionamide-primed mesenchymal stem cells, the expression of amyloid 13 significantly decreased.

In addition, ethionamide-primed or unprimed mesenchymal stem cells (hMSCs) were administered to a ventricle of a mouse using the same dementia mouse as described above, and the brain was extracted one week after administration. Subsequently, ELISA was performed using a sample obtained by homogenization of the extracted brain to measure an amyloid 13 protein level. Here, the tissue sample was separated into a soluble fraction and an insoluble fraction to confirm an amyloid 13 level.

Figure 5B:
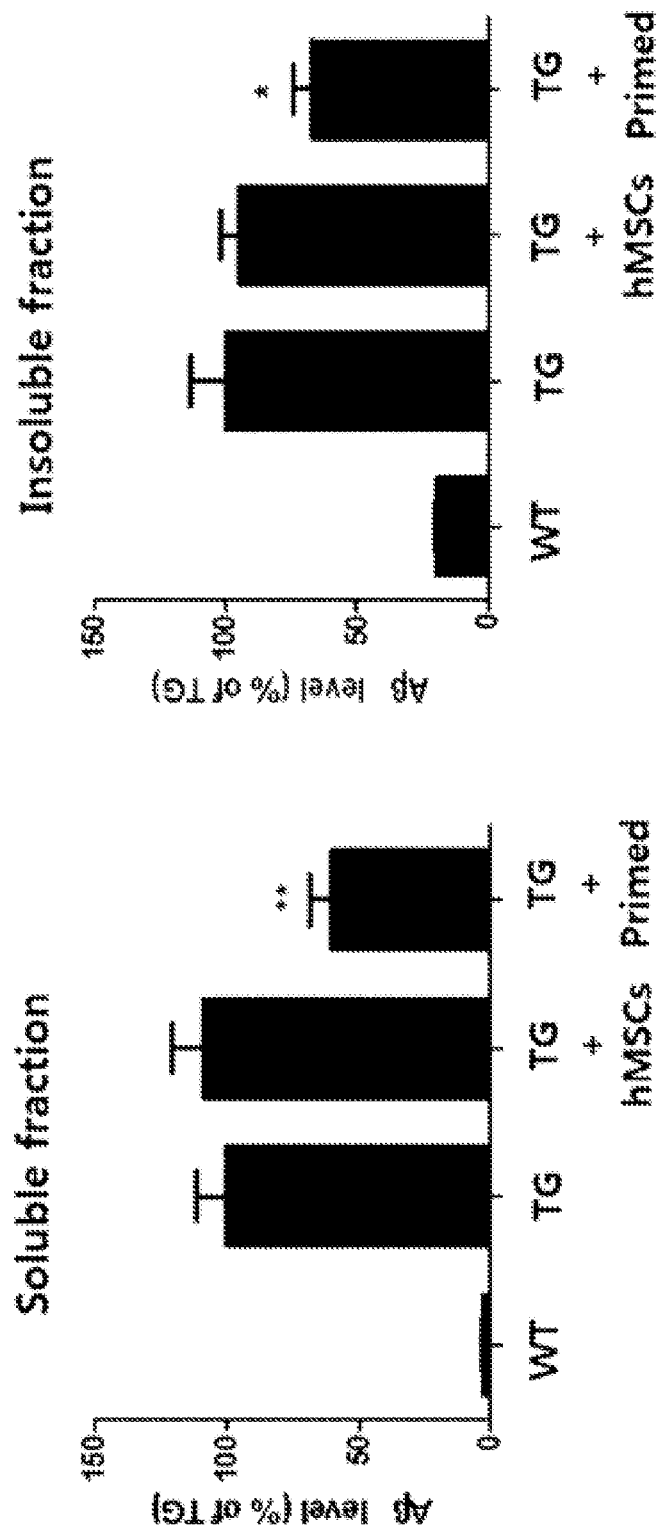
FIG. 5B shows amyloid 13 levels measured by ELISA using soluble fractions and insoluble fractions obtained by homogenizing brain tissue after mesenchymal stem cells are administered to a dementia mouse model by the same method as used in FIG. 5A.

As a result, as shown in FIG. 5B, it was confirmed that, compared with a control or the group co-cultured with ethionamide-unprimed mesenchymal stem cells, in the group co-cultured with ethionamide-primed mesenchymal stem cells, amyloid 13 expression significantly decreases.

Through the above-described experiments, it can be seen that ethionamide-primed stem cells have an effect of reducing amyloid 13, indicating that the stem cells have a therapeutic effect by reducing the pathology of a degenerative brain disease.

Example 8. Confirmation of Encephalopathy-Reducing Effect by Ethionamide-Primed Stem Cells in Dementia Mouse Model Based on the results obtained in Example 7, it was intended to examine whether ethionamide-primed stem cells have an effect of reducing encephalopathy in a dementia mouse model. To this end, by the same method as in FIG. 7, in a dementia mouse model, ethionamide-primed or unprimed mesenchymal stem cells (hMSCs) were administered to a ventricle of the mouse, and the brain was extracted one week after administration, followed by fixing with 4% paraformaldehyde. Subsequently, a tissue section obtained by processing brain tissue was treated with an encephalopathy-related antibody, glial fibrillary acidic protein (GFAP), for immunostaining, and then observed using a fluorescence microscope. In addition, fluorescence intensities were quantified and compared.

Figure 6:
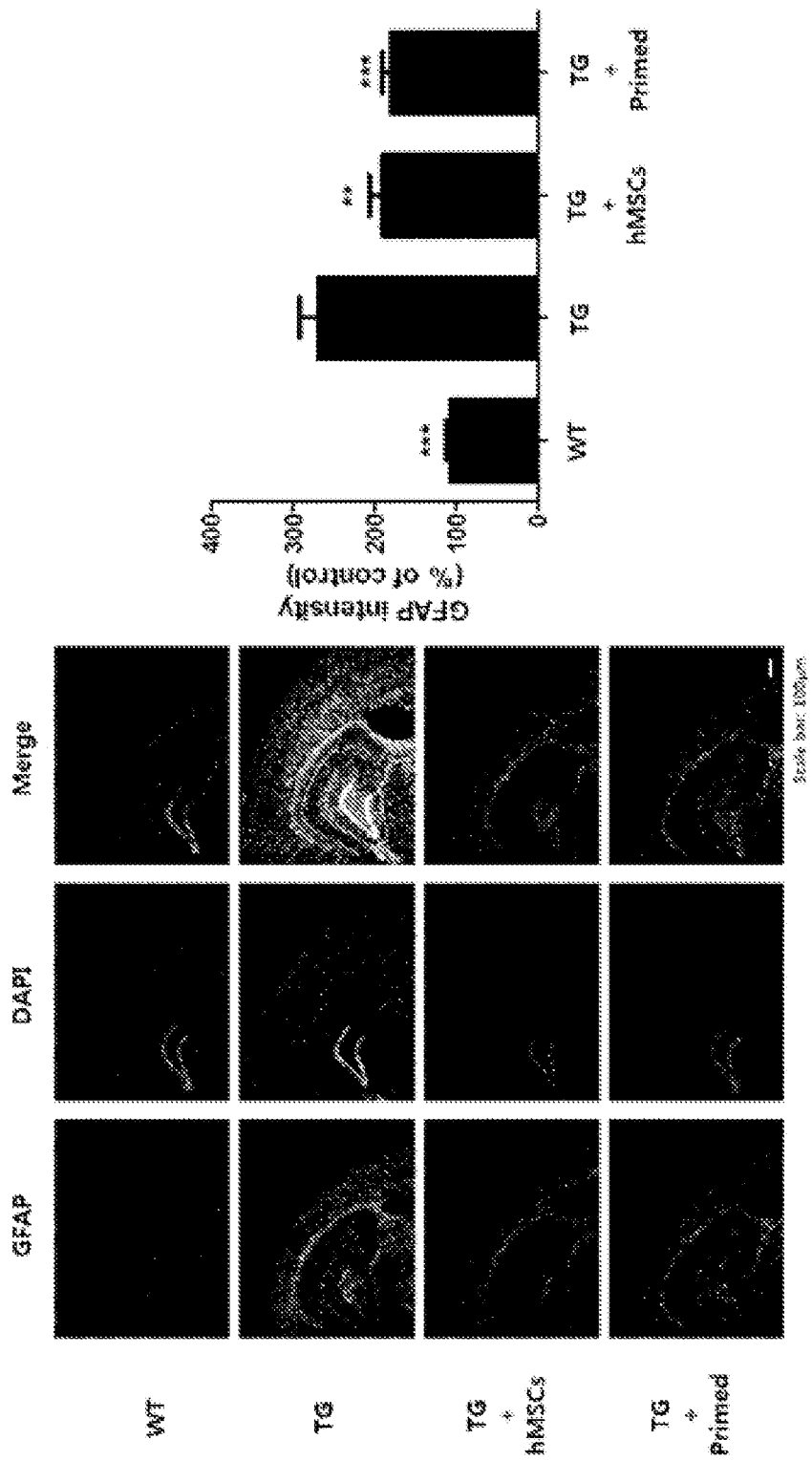
FIG. 6 shows results of immunostaining performed on brain tissue sections obtained by the same method as used in FIG. 5A using an encephalopathy-associated antibody (GFAP), and the quantification result thereof.

As a result, as shown in FIG. 6, compared with a wild-type mouse (WT), in an intact dementia mouse, it was confirmed that GFAP expression significantly increases. On the contrary, when ethionamide-primed or unprimed mesenchymal stem cells were administered, GFAP expression decreased, and particularly, when ethionamide-primed mesenchymal stem cells were administered, the GFAP expression decreased at a higher level.

From such a result, it can be seen that the ethionamide-primed stem cells have an effect of reducing encephalopathy.

Example 9. Confirmation of Tau-Reducing Effect by Ethionamide-Primed Stem Cells in Dementia Mouse Model Further, based on the results of Example 7 and 8, the inventors intended to examine whether the ethionamide-primed stem cells according to the present invention have an effect of reducing tau protein, which is another pathological symptom, in a dementia mouse model. Specifically, in the dementia mouse model, ethionamide-primed or unprimed mesenchymal stem cells (hMSCs) were administered to a ventricle of the mouse, and the brain was extracted two weeks after administration and then homogenized. Afterward, ELISA was performed using the obtained brain tissue sample to measure the expression level of the tau protein. Here, an amount of tau with phosphorylated threonine residues 181 and 231 of the tau protein was confirmed.

Figure 7:
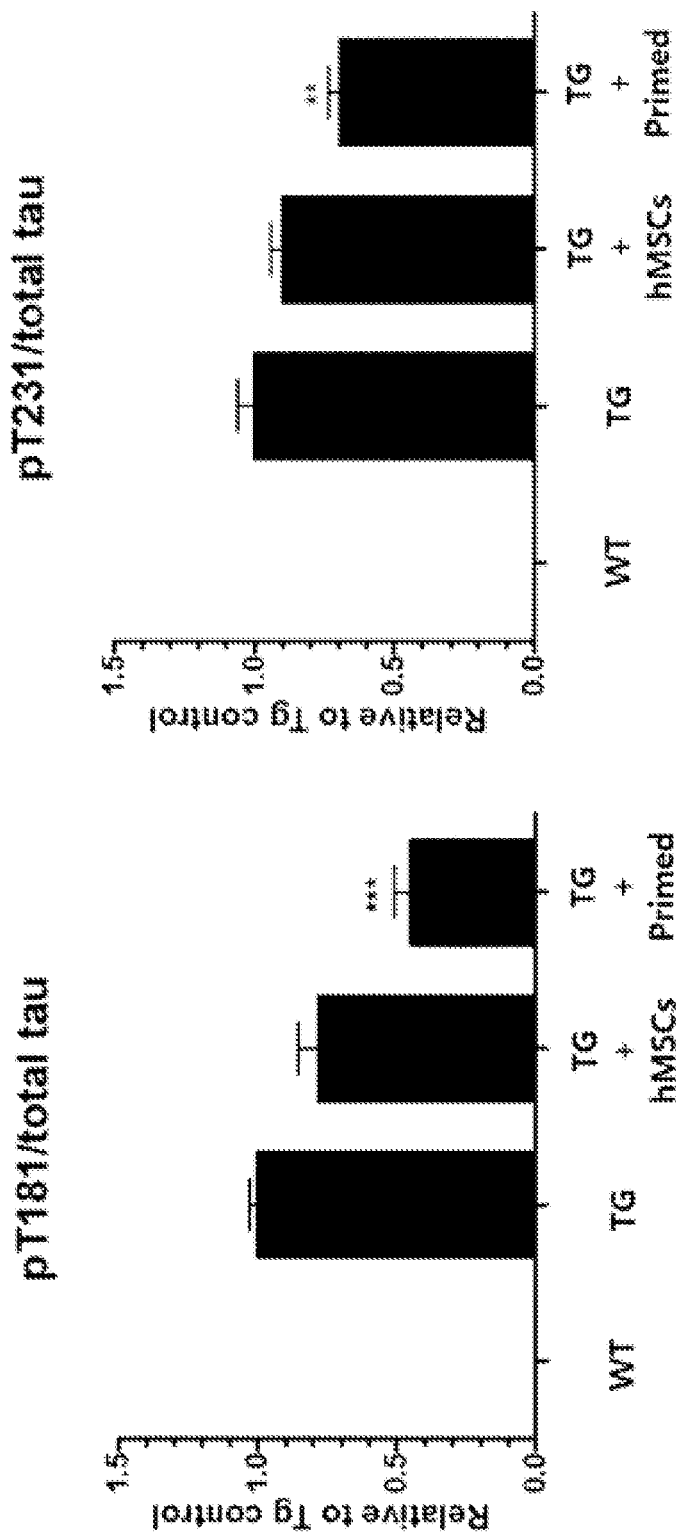
FIG. 7 shows the levels of tau proteins in which threonine residues 181 and 231 are phosphorylated through ELISA performed on brain tissue samples obtained two weeks after ethionamide-primed or unprimed mesenchymal stem cells are administered to a ventricle of dementia mouse model by the same method as used in FIG. 5B.

As an analysis result, as shown in FIG. 7, compared with a control or the group co-cultured with ethionamide-unprimed mesenchymal stem cells, in the group co-cultured with ethionamide-primed mesenchymal stem cells, it was confirmed that the expression of phosphorylated tau significantly decreased.

It should be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limiting in any aspect.

INDUSTRIAL APPLICABILITY

It was confirmed that ethionamide according to the present invention reinforces the efficacies of stem cells such as the anti-inflammatory effect and paracrine effect of stem cells, and the ethionamide-primed stem cells exhibit a therapeutic effect through substantial lesion improvement in a dementia model, and thus ethionamide and the ethionamide-primed stem cells which are reinforced in various efficacies are expected to be used in various fields including the development of therapeutic agents for an inflammatory disease and a degenerative brain disease.

What is claimed is:

1. A method of reinforcing the efficacy of mesenchymal stem cells, comprising:
   culturing stem cells for 72 hours in a medium comprising 10-200 μM ethionamide,
   wherein the efficacy reinforcement is an improvement in expression of a paracrine factor in the stem cells, and
   wherein the paracrine factor is one or more selected from the group consisting of a brain-derived neurotrophic issue (BDNF), a vascular endothelial cell growth factor (VEGF), insulin-like growth factor-1 (IGF-1), a hepatocyte growth factor (HGF), heme oxygenase-1 (HO-1), NAD(P)H:quinone oxidoreductase (NQO1), a glutamate-cysteine ligase catalytic subunit (GCLC) and a glutamate-cysteine ligase modifier subunit (GCLM).

2. The method of claim 1, wherein the mesenchymal stem cells are derived from one or more tissues selected from the group consisting of the umbilical cord, bone marrow, fat, muscle, nerve, skin, the amnion and the placenta.

3. A method of treating a degenerative brain disease, comprising:
   administering to a subject in need thereof an effective amount of the stem cells with reinforced efficacy, which are prepared by the method of claim 1 as an active ingredient,
   wherein the degenerative brain disease is selected from the group consisting of dementia, Alzheimer's disease, and frontotemporal dementia.

\* \* \* \* \*